US006300118B1

(12) United States Patent
Chavez et al.

(10) Patent No.: US 6,300,118 B1
(45) Date of Patent: Oct. 9, 2001

(54) PLASMIDS COMPRISING A GENETICALLY ALTERED FELINE IMMUNODEFICIENCY VIRUS GENOME

(75) Inventors: Lloyd Chavez, Highlands Ranch, CO (US); Terri Wasmoen; Chengjin Huang, both of Fort Dodge, IA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 08/479,703

(22) Filed: Jun. 7, 1995

(51) Int. Cl.[7] ............................. C12N 15/63; C12N 1/21; C07H 21/04

(52) U.S. Cl. .................................... 435/252.3; 435/320.1; 435/235; 435/236; 435/440; 435/445; 435/471; 435/475; 435/476; 536/23.72

(58) Field of Search ................................ 435/240.2, 69.1, 435/243, 235.1, 320.1, 440, 445, 471, 475, 476, 252.3, 235, 236; 536/23.72, 22.1; 935/23, 32

(56) References Cited

U.S. PATENT DOCUMENTS

| | | | |
|---|---|---|---|
| 5,037,753 | 8/1991 | Pedersen et al. | 435/5 |
| 5,118,602 | 6/1992 | Pedersen et al. | 435/5 |

(List continued on next page.)

FOREIGN PATENT DOCUMENTS

| | | |
|---|---|---|
| 0 576 092 A1 | 12/1993 | (EP) . |
| WO 90/13573 | 11/1990 | (WO) . |

(List continued on next page.)

OTHER PUBLICATIONS

Morikawa, et al., Analyses of the Requirements for the Synthesis of Virus–like Particles by Feline Immunodeficiency Virus Gag Using Baculovirus Vectors, Virology, 183:288–297 (1991).

Yamamoto et al., *J. Virol.* 57:601, 1993.

Hosie et al., in *Abstracts of the International Sympsoium on Feline Retrovirus* Research, 1993, p. 50.

(List continued on next page.)

*Primary Examiner*—Carla J. Myers
(74) *Attorney, Agent, or Firm*—Darby & Darby

(57) ABSTRACT

The present invention pertains to the prevention or lessening of disease in cats caused by Feline Immunodeficiency Virus (FIV). Prevention or lessening of disease is understood to mean the amelioration of any symptoms, including immune system disruptions, that result from FIV infection. The invention provides for a plasmid which encodes the FIV genome where said genome has had a portion of the gag gene, specifically the p10 (nucleocapsid) coding region, or a portion thereof, deleted. This deletion prevents the production of functional or whole p10 protein, which in turn, prevents the packaging of RNA into virions produced from transfection of this plasmid into an appropriate host cell, resulting in virions which do not contain RNA. Such virions will be described as "empty" virions. The invention also encompasses host cells transformed with the plasmid which produce the empty virions, and the empty virions themselves. In another embodiment, the invention encompasses vaccines that comprise one or more empty virions described above, with a pharmaceutically acceptable carrier or diluent and a pharmaceutically acceptable adjuvant. In yet another aspect, the invention provides methods for preventing or lessening disease caused by FIV, which is carried out by administering to a feline in need of such treatment the vaccines described above.

4 Claims, 10 Drawing Sheets

U.S. PATENT DOCUMENTS

| | | |
|---|---|---|
| 5,177,014 | 1/1993 | O'Conner et al. ............... 435/5 |
| 5,219,725 | 6/1993 | O'Conner et al. ............... 435/5 |
| 5,252,348 | 10/1993 | Schreier et al. ............... 424/450 |
| 5,256,767 | 10/1993 | Salk et al. ............... 530/350 |
| 5,275,813 | 1/1994 | Yamamoto et al. ............... 424/89 |
| 5,324,643 | 6/1994 | Greatbatch et al. ............... 435/91.32 |
| 5,324,664 | 6/1994 | Nunberg et al. ............... 435/320.1 |
| 5,674,720 * | 10/1997 | Gorelick ............... 435/172.3 |

FOREIGN PATENT DOCUMENTS

| | | |
|---|---|---|
| WO 92/09632 | 6/1992 | (WO). |
| WO 92/15684 | 9/1992 | (WO). |
| WO 93/01278 | 1/1993 | (WO). |
| WO 93/05789 | 4/1993 | (WO). |
| WO 93/08836 | 5/1993 | (WO). |
| WO 93/17706 | 9/1993 | (WO). |
| WO 94/02612 | 2/1994 | (WO). |
| WO 94/02613 | 2/1994 | (WO). |
| WO 94/06471 | 3/1994 | (WO). |
| WO 94/06921 | 3/1994 | (WO). |
| WO 94/20622 | 9/1994 | (WO). |
| WO 95/05460 | 2/1995 | (WO). |

OTHER PUBLICATIONS

Tompkins et al., *J. Am. Vet Med. Assoc.* 199: 1311, 1991 . . . ?.

Mackett and Smith, *J Gen Virol* 67:2067–2082, 1986.

Wasmoen et al., *Vet. Immuno. Immunopath.* 35:83 1992.

Tompkins et al. *Vet. Immunol. Immunopathol.* 26:305, 1990.

R.V. English et al. *J. Infect. Dis.* 170:543, 1994.

Davidson et al., *Am. J. Pathol.* 143:1486, 1993.

* cited by examiner

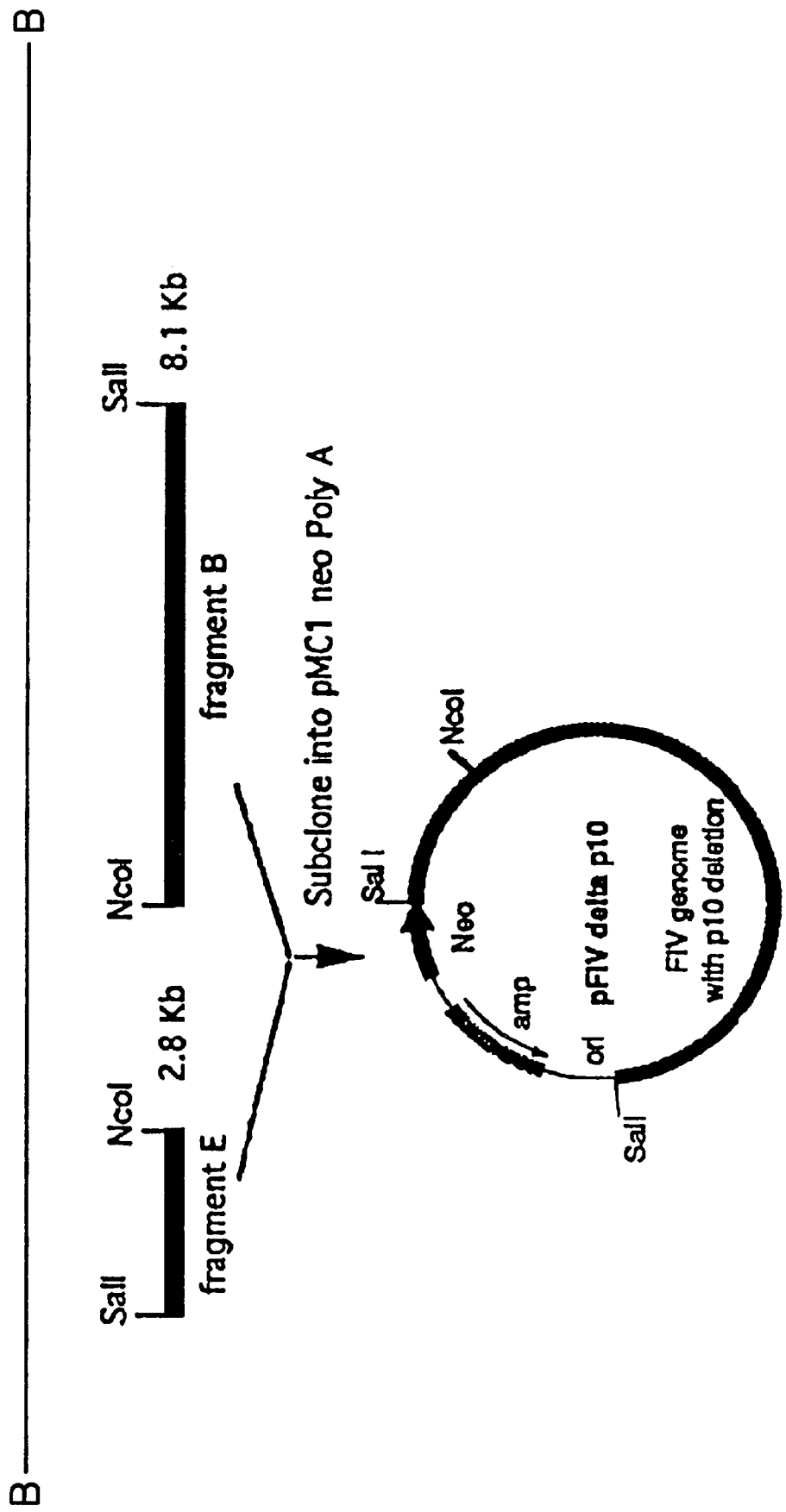
FIG. IC

FIG. 2A

```
         10         20         30         40         50         60
          *          *          *          *          *          *
ATGGGGAATG GACAGGGGCG AGATTGGAAA ATGGCCATTA AGAGATGTAG TAATGCTGCT
TACCCCTTAC CTGTCCCCGC TCTAACCTTT TACCGGTAAT TCTCTACATC ATTACGACGA
- - - - -> p15 Matrix protein 70         80         90        100        110        120
          *          *          *          *          *          *
GTAGGAGTAG GGGGGAAGAG TAAAAAATTT GGGGAAGGGA ATTTCAGATG GGCCATTAGA
CATCCTCATC CCCCCTTCTC ATTTTTTAAA CCCCTTCCCT TAAAGTCTAC CCGGTAATCT 130        140        150        160        170        180
          *          *          *          *          *          *
ATGGCTAATG TATCTACAGG ACGAGAACCT GGTGATATAC CAGAGACTTT AGATCAACTA
TACCGATTAC ATAGATGTCC TGCTCTTGGA CCACTATATG GTCTCTGAAA TCTAGTTGAT 190        200        210        220        230        240
          *          *          *          *          *          *
AGGTTGGTTA TTTGCGATTT ACAAGAAAGA AGAAAAAAAT TTGGATCTTG CAAAGAAATT
TCCAACCAAT AAACGCTAAA TGTTCTTTCT TCTTTTTTTA AACCTAGAAC GTTTCTTTAA 250        260        270        280        290        300
          *          *          *          *          *          *
GATAAGGCAA TTGTTACATT AAAAGTCTTT GCGGCAGTAG GACTTTTAAA TATGACAGTG
CTATTCCGTT AACAATGTAA TTTTCAGAAA CGCCGTCATC CTGAAAATTT ATACTGTCAC
```

FIG. 2C

```
       610        620        630        640        650        660
        *          *          *          *          *          *
GAAATATTGG ATGAAAGCTT AAAGCAACTT ACTGCAGGAT ATGATCGTAC ACATCCCCCT
CTTTATAACC TACTTTCGAA TTTCGTTGAA TGACGTCCTA TACTAGCATG TGTAGGGGGA 670        680        690        700        710        720
        *          *          *          *          *          *
GATGCTCCCA GACCATTACC CTATTTACT GCAGCAGAAA TTATGGGTAT TGGATTTACT
CTACGAGGGT CTGGTAATGG GATAAAATGA CGTCGTCTTT AATACCCATA ACCTAAATGA 730        740        750        760        770        780
        *          *          *          *          *          *
CAAGAACAAC AAGCAGAAGC AAGATTTGCA CCAGCTAGGA TGCAGTGTAG AGCATGGTAT
GTTCTTGTTG TTCGTCTTCG TTCTAAACGT GGTCGATCCT ACGTCACATC TCGTACCATA 790        800        810        820        830        840
        *          *          *          *          *          *
CTCGAGGGAC TAGGAAAATT GGGCGCCATA AAAGCTAAGT CTCCTCGAGC TGTGCAGTTA
GAGCTCCCTG ATCCTTTTAA CCCGCGGTAT TTTCGATTCA GAGGAGCTCG ACACGTCAAT 850        860        870        880        890        900
        *          *          *          *          *          *
AGACAAGGAG CTAAGGAAGA TTATTCATCC TTTATTGACA GATTGTTTGC CCAAATAGAT
TCTGTTCCTC GATTCCTTCT AATAAGTAGG AAATAACTGT CTAACAAACG GGTTTATCTA
```

FIG. 2D

```
     910        920        930        940        950        960
      *          *          *          *          *          *
CAAGAACAAA ATACAGCTGA AGTTAAGTTA TATTTAAAAC AGTCATTAAG CATGGCTAAT
GTTCTTGTTT TATGTCGACT TCAATTCAAT ATAAATTTTG TCAGTAATTC GTACCGATTA 970        980        990       1000       1010       1020
      *          *          *          *          *          *
GCTAATGCAG AATGTAAAAA GCCAATGACC CACCTTAAGC CAGAAAGTAC CCTAGAAGAA
CGATTACGTC TTACATTTTT CGGTTACTGG GTGGAATTCG GTCTTTCATG GGATCTTCTT 1030       1040       1050       1060       1070       1080
      *          *          *          *          *          *
AAGTTGAGAG CTTGTCAAGA AATAGGCTCA CCAGGATATA AAATGCAACT CTTGGCAGAA
TTCAACTCTC GAACAGTTCT TTATCCGAGT GGTCCTATAT TTTACGTTGA GAACCGTCTT
                                                p25 <-----

1090       1100       1110       1120       1130       1140
      *          *          *          *          *          *
GCTCTTACAA AAGTTCAAGT AGTGCAATCA AAAGGATCAG GACCAGTGTG TTTTAATTGT
CGAGAATGTT TTCAAGTTCA TCACGTTAGT TTTCCTAGTC CTGGTCACAC AAAATTAACA
-----> p10 Nucleocapsid 1150       1160       1170       1180       1190       1200
      *          *          *          *          *          *
AAAAAACCAG GACATCTAGC AAGACAATGT AGAGAAGTGA GAAAATGTAA TAAATGTGGA
TTTTTTGGTC CTGTAGATCG TTCTGTTACA TCTCTTCACT CTTTTACATT ATTTACACCT
```

FIG. 2E

```
         1210          1220          1230          1240          1250          1260
           *             *             *             *             *             *
    AAACCTGGTC    ATGTAGCTGC    CAAATGTTGG    CAAGGAAATA    GAAAGAATTC    GGGAAACTGG
    TTTGGACCAG    TACATCGACG    GTTTACAACC    GTTCCTTTAT    CTTTCTTAAG    CCCTTTGACC
                                                                          -----> POL 1270          1280          1290          1300          1310          1320
           *             *             *             *             *             *
    AAGGCGGGGC    GAGCTGCAGC    CCCAGTGAAT    CAAGTGCAGC    AAGCAGTAAT    GCCATCTGCA
    TTCCGCCCCG    CTCGACGTCG    GGGTCACTTA    GTTCACGTCG    TTCGTCATTA    CGGTAGACGT 1330          1340          1350
           *             *             *
    CCTCCAATGG    AGGAGAAACT    ATTGGATTTA    TAA
    GGAGGTTACC    TCCTCTTTGA    TAACCTAAAT    ATT
                                p10 <------
                                           POL ----->
```

FIG. 3A

```
M G N G Q G R D W K M A I K R C S N A A
-----> p15 Matrix protein
V G V G K S T G K R E P K F G E N F R W A I R
M A N V I C D L T V F G R K K A V F E T L D Q L
R L V A I V T A A Q M F G L L N M T V K E I
D K S A A A G K E G P A F T R P S
S M K E A G G K E P P Q A F P I Q T V
                    p15 <----- ----> p25 Capsid protein
N G V P Q Y V A L D P K M V S I F M E K
A R E G L G G E V H E L L W F T A F S A N
L T P T D M A T L K Q L T M A A P G C A D K
E I L D E S L P Y F T A A E I M G I G R T H P P
D A P R L P Y F T A A E I M G I G F T
```

```
Q E Q A E A R F A P A R M Q C R A W Y
L E Q L G K L G A I K A K S P R A W Q L
R Q R Q A N T A E D Y S S F I D R L F A Q I D
Q E Q E A N T A E V K L Y L K Q S L M A N
A A N A E C K K P M T H L K P E S T L E E
K L R A C Q E I G S P G Y K M Q L L A E
A L T K V Q V V Q S                     G P   V C F N C
        ----> p10 Nucleocapsid                p25 <------
K K P G H L A R Q C R E V R K C N K C G
K P G H V A A K C W Q G N R       K N S G N W
                                  K E F G K L
                                  ----> POL (-1 ORF)

K A G R A A A P V N Q V Q Q A V M P S A
E G G A S C S P S E S S A A S S N A I C
P P M E E K L L D L
T S N G G E T I G F I
            p10 <------
            POL ------>
```

PLASMIDS COMPRISING A GENETICALLY ALTERED FELINE IMMUNODEFICIENCY VIRUS GENOME

FIELD OF THE INVENTION

The present invention pertains to the prophylaxis and treatment of disease caused by feline immunodeficiency virus (FIV), using genetically altered FIV virions. Specifically, a portion of the p10 gene, which encodes a protein responsible for packaging of the RNA into the virion, has been deleted. The resulting virions are produced in appropriate host cell lines and used to make vaccines comprising whole killed virions which do not comprise viral RNA.

BACKGROUND OF THE INVENTION

Feline immunodeficiency virus (FIV) infection is a significant health problem for domestic cats around the world. As in its human counterpart, infection with FIV causes a progressive disruption in immune function. In the acute phase of infection, the virus causes transient illness associated with symptoms such as lymphadenopathy, pyrexia, and neutropenia. Subsequently, an infected animal enters an asymptomatic phase of 1–2 years before clinical manifestations of immune deficiency become apparent, after which the mean survival time is usually less than one year.

FIV is a typical retrovirus that contains a single-stranded polyadenylated RNA genome, internal structural proteins derived from the gag gene product, and a lipid envelope containing membrane proteins derived from the env gene product (Bendinelli et al., *Clin.Microbiol.Rev.* 8:87, 1995). The gag gene is translated into a primary product of about 50 kDa that is subsequently cleaved by a viral protease into the matrix (p15), capsid (p25), and nucleocapsid (p10) proteins. The start and the end for each cleavage product of the GAG polyprotein are indicated in FIGS. 2A–2E underneath the open reading frame. The env gene yields a primary translation product of 75–80 kDa (unglycosylated molecular weight); in infected cells, the precursor has an apparent molecular weight of 145–150 kDa due to N-linked glycosylation. The env precursor is cleaved in the Golgi apparatus into the SU and TM proteins (also designated gp95 and gp40, respectively).

As discussed above, the gag gene of the feline immunodeficiency virus (FIV) is initially translated as a precursor polyprotein which is cleaved to yield the functionally mature matrix protein, capsid protein and nucleocapsid protein making up the core of virus (Elder et al., *J. Virol.* 67: 1869–76, 1993). The pot gene overlaps the gag gene by 112 nucleotides, and is in a −1 reading frame with respect to that of the gag gene. Thus, the gene is translated as a Gag-Pol fusion protein produced by ribosome frameshifting. The overlapping region contains frameshift signals, GGGAAAC and GGAGAAAC, located at the 3' end of the gag gene (Morikawa et al., *Virol.* 186: 389–97, 1992).

The nucleocapsid protein, or p10, is a small basic protein, which is associated with the genomic RNA and may be required for viral RNA packaging (Egberink et al. *J. Gen. Virol.* 71: 739–743, 1990; Steinman et al., *J. Gen. Virol.* 71: 701–06, 1990). The p10 protein contains two cysteine arrays each consisting of 14 amino acid residues with the sequence C—$X_2$—C—$X_4$—H—$X_4$—C (where X represents any amino acid and the subscript is the number of residues). Genetic studies with other retroviruses have shown that these two cysteine arrays are essential for viral RNA packaging (Rein et al., *J. Virol.* 68: 6124–29, 1994; Meric et al., *J. Virol.* 62: 3328–33; Gorelick et al., *Proc. Natl. Acad. Sci. USA* 85:8420–24, 1988). Therefore, deletion of these two cysteine arrays should, in theory, generate FIV virus particles which contains all viral proteins, but no viral genomic RNA. These FIV viral particles should be non-infectious and could be used to effect efficacious immune protection in vaccinated cats.

Most vaccines against FIV have failed to induce protective immunity. Ineffective vaccines have involved inactivated whole virus, fixed infected cells, recombinant CA and SU proteins, and a synthetic peptide corresponding to the V3 region of SU. In some cases, the vaccine actually enhanced infection after challenge. In one system, vaccination with paraformaldehyde-fixed virus or infected cells resulted in protective immunity (Yamamoto et al., *J. Virol.* 67:601, 1993), but application of this approach by others was unsuccessful (Hosie et al., in Abstracts of the International Symposium on Feline Retrovirus Research, 1993, page 50).

Thus, there is a need in the art for an effective whole killed virion vaccine against FIV.

SUMMARY OF THE INVENTION

The present invention pertains to the prevention or lessening of disease in cats caused by Feline Immunodeficiency Virus (FIV). Prevention or lessening of disease is understood to mean the amelioration of any symptoms, including immune system disruptions, that result from FIV infection.

The invention provides for a plasmid which encodes the FIV genome where said genome has had a portion of the gag gene, specifically the p10 (nucleocapsid) coding region, or a portion thereof, deleted. This deletion prevents the production of functional or whole p10 protein, which in turn, prevents the packaging of RNA into virions produced from transfection of this plasmid into an appropriate host cell, resulting in virions which do not contain RNA. Such virions will be described as "empty" virions. The invention also encompasses host cells transformed with the plasmid which produce the empty virions, and the empty virions themselves.

In another embodiment, the invention encompasses vaccines that comprise one or more empty virions described above, with a pharmaceutically acceptable carrier or diluent and a pharmaceutically acceptable adjuvant.

In yet another aspect, the invention provides methods for preventing or lessening disease caused by FIV, which is carried out by administering to a feline in need of such treatment the vaccines described above.

BRIEF DESCRIPTION OF THE DRAWINGS

FIGS. 1A–1C are graphic illustration of the cloning strategy for creating FIV with deletion of p10.

FIGS. 2A–2E shows the DNA sequence of the gag gene of FIV SEQ ID. NO. 5, with the delineations of the coding sequence for the various proteolytic products indicated. The double underlined DNA sequence is deleted in a preferred embodiment of the present invention. The gag-pol frameshift start site is indicated by single underlining.

FIGS. 3A–3B show the protein sequences for the translation products of the gag gene of FIV, including both the primary SEQ ID. NO. 6 and secondary SEQ ID. NO. 7 open reading frames. The double underlined amino acids are not encoded by a preferred embodiment of the present invention.

DETAILED DESCRIPTION OF THE INVENTION

All patents, patent applications, and references cited herein are hereby incorporated by reference in their entirety.

In the case of inconsistencies, the present disclosure, including definitions, will control.

Figure 1A:
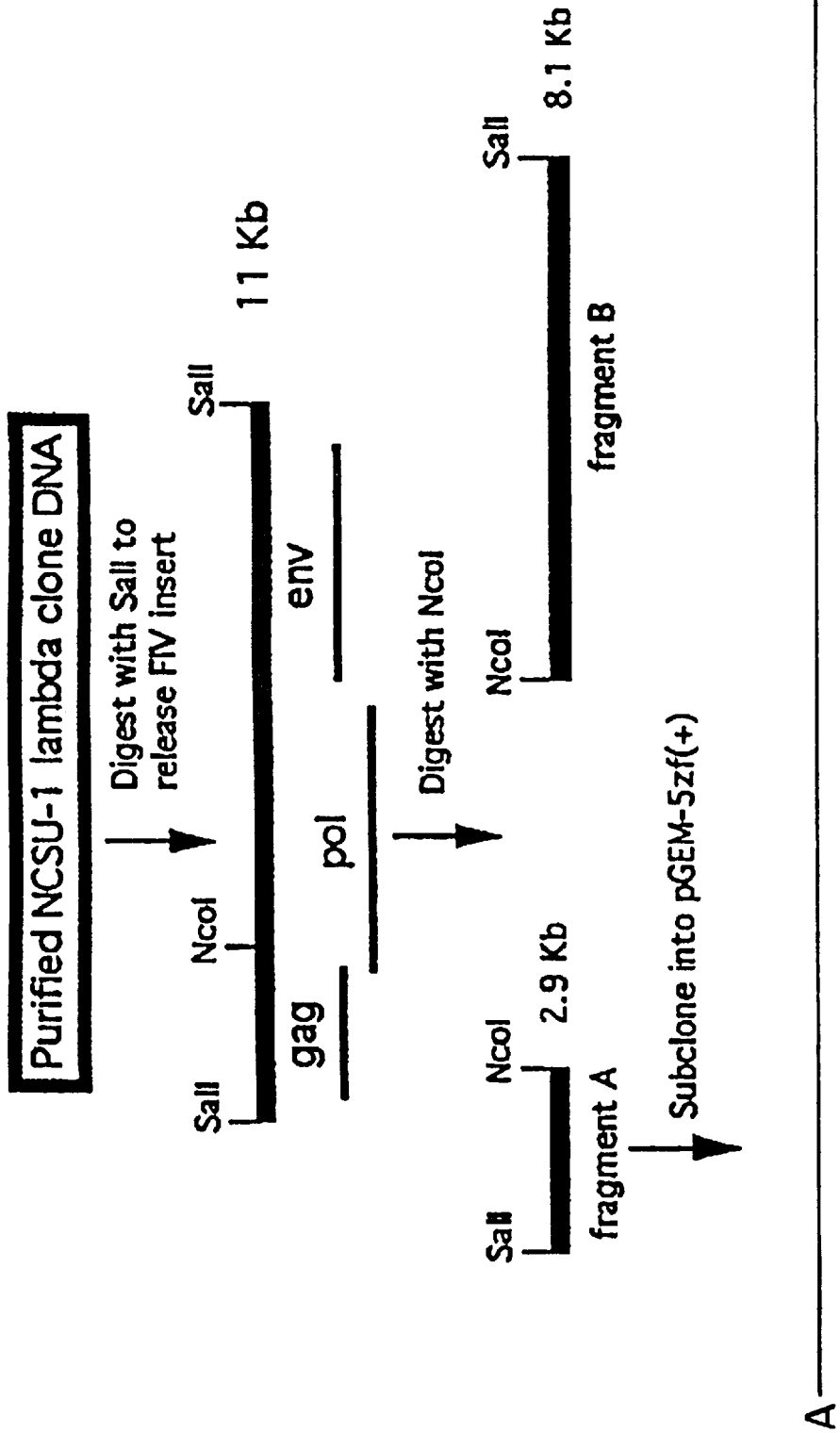
Figure 1B:
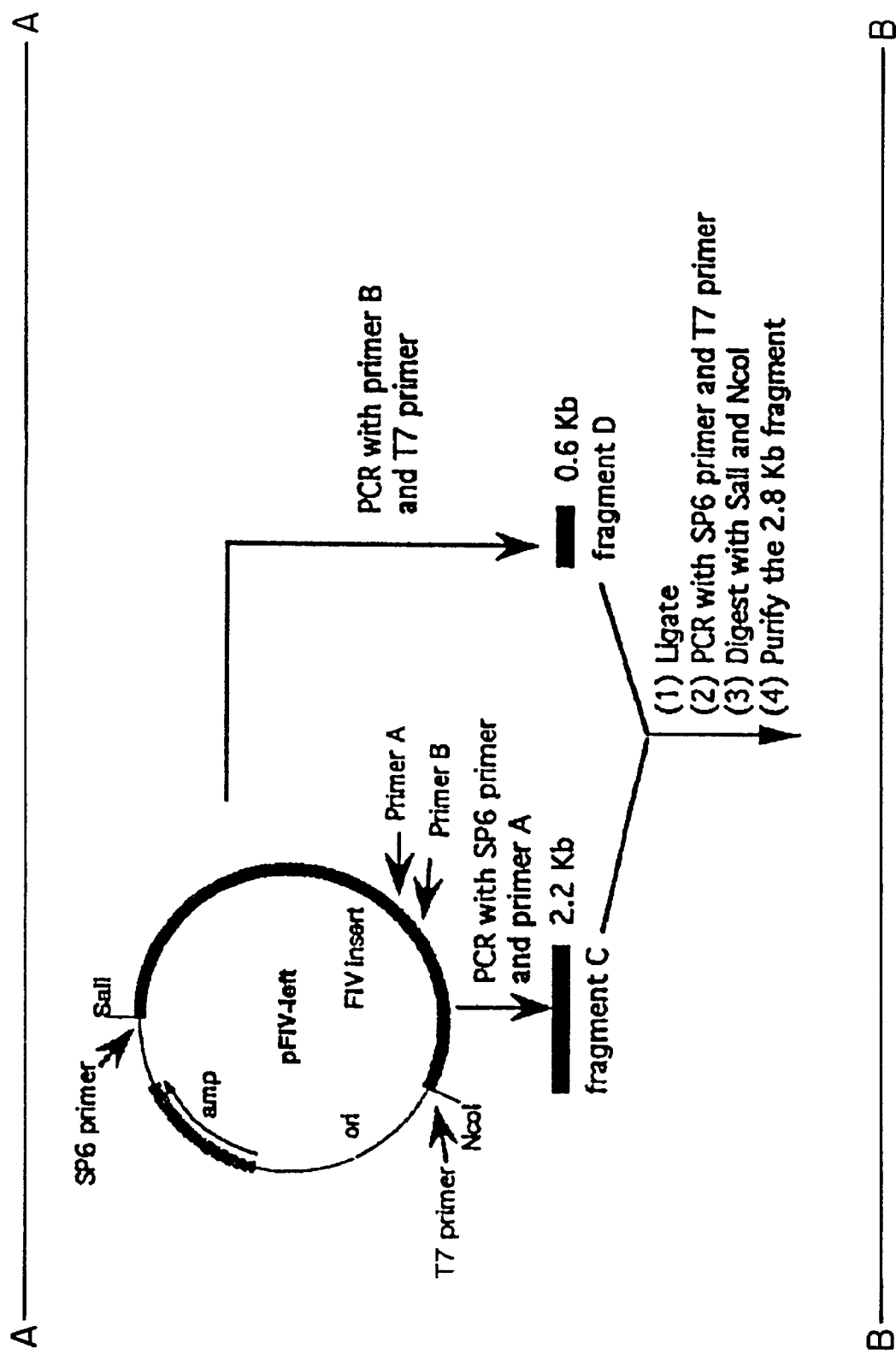
Figure 2B:
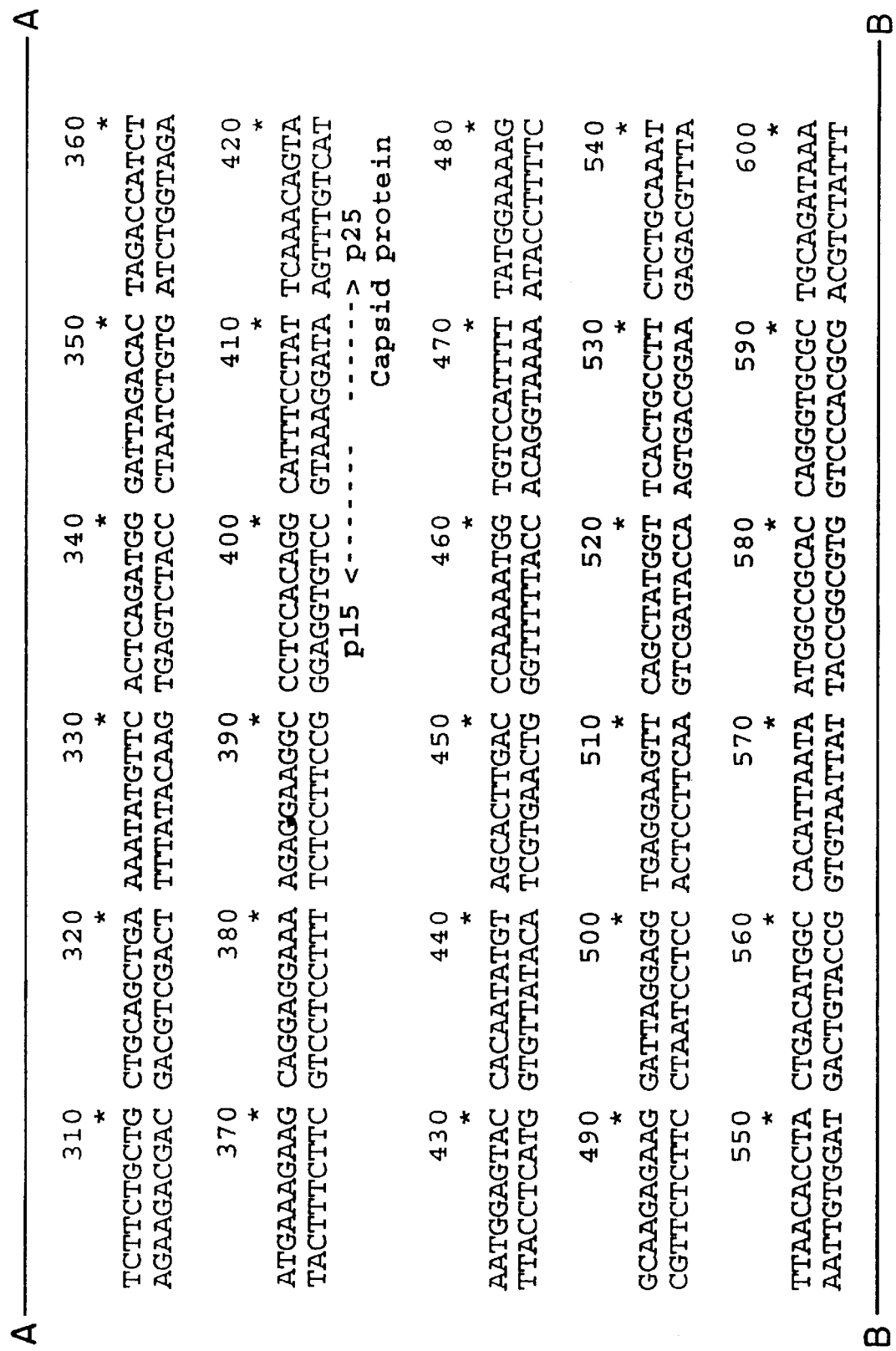

The vaccine of the present invention may be prepared by creating a recombinant FIV carrying a deletion of the p10 gene, or a portion thereof, encoding a portion of the gag protein of Feline Immunodeficiency Virus (FIV). The cloning scheme employed to produce the deleted virus eliminates 39 codons which include the two cysteine arrays within the p10 gene without disrupting either the gag gene open reading frame or the gag-pol frameshifting as occurs in the wild type virus-infected cells. The two cysteine arrays are highlighted in FIGS. 2A–2E, where cysteine array 1 encompasses nucleotides 1129 to 1170 and cysteine array 2 encompasses nucleotides 1186 to 1227. The thirty nine codons and amino acids which are deleted are double underlined in FIGS. 2 and 3. The deletion does not disrupt the original p10 open reading frame. The deletion also does not alter the gag-pol frameshift start site and frameshift signal. Therefore, in theory, the frequency of gag-pol frameshifting at nucleotide 1242 should not be affected by the deletion of the 39 codons preceding the gag-pol frameshift start site. FIGS. 2A–2E indicate the gag-pol frameshift start site by single underlining. FIGS. 2A–2E indicate the 5' end of the POL polyprotein underneath the p10 open reading frame, while FIGS. 3A–3B list the amino acid sequence of p10 and the frameshifted POL protein.

The process for constructing the p10 deletion vaccine is outlined as follows. A plasmid construct is made which deletes a portion of the p10 encoding gene sequences using PCR-mediated mutagenesis. The construct is designed to not delete any of the 112 nucleotides (1243 to 1353) which overlap the gag and pol genes and to not eliminate the frameshift signal which is necessary for pol transcription. Once constructed, the plasmid is transfected into an appropriate host cell, such as mammalian cells, and the transformed cells are screened for non-infectious virus production. Cells which prove to produce non-infectious (presumably empty) virions are used to produce high levels of virus particles, which are isolated from the cell culture medium.

Although this particular construct and method are effective in producing empty virions, i.e., those which do not contain RNA, one of ordinary skill in the art would recognize alternative well-known methods of achieving the same goal. For example, the deletion need not eliminate the whole p10 encoding sequence, only enough sequence for the function of the protein to be eliminated. One representative example of this approach would be deletion of only one of the two cysteine arrays. Further, fragments of sequence need not be deleted. Any genetic alteration, i.e., site-directed mutagenesis of cysteines within the array, using methods well known in the art can be employed to construct a FIV genome which encodes empty virions. Thus, well-known variants of the genetic alterations presently employed which result in genomes which encode empty virions are contemplated to be within the scope of the present invention.

The isolated virus may be stored after concentration at 4° C. or frozen (–50° C. or colder) or lyophilized until the time of use. Compounds such as NZ-amine, dextrose, gelatin or others designed to stabilize the virus during freezing and lyophilization may be added. The virus may be concentrated using commercially available equipment. To produce the vaccine, isolated particles can be chemically treated to ensure lack of infectivity, that is, inactivated and mixed with an adjuvant(s).

Typically, the concentration of virus in the vaccine formulation will be a minimum of $10^{6.0}$ virus particles per dose, but will typically be in the range of $10^{6.0}$ to $10^{8.0}$ virus particles per dose. At the time of vaccination, the virus is thawed (if frozen) or reconstituted (if lyophilized) with a physiologically-acceptable carrier such as deionized water, saline, phosphate buffered saline, or the like. An additional optional component of the present vaccine is a pharmaceutically acceptable adjuvant. Non-limiting examples of suitable adjuvants include squalane and squalene (or other oils of animal origin); block copolymers such as Pluronic® (L121) Saponin; detergents such as Tween®-80; Quil® A, mineral oils such as Drakeol® or Marcol®, vegetable oils such as peanut oil; Corynebacterium-derived adjuvants such as corynebacterium parvum; Propionibacterium-derived adjuvants such as Propionibacterium acne; *Mycobacterium bovis* (Bacillus Calmette and Guerinn, or BCG); interleukins such as interleukin 2 and interleukin-12; monokines such as interleukin 1; tumor necrosis factor; interferons such as gamma interferon; combinations such as saponin-aluminum hydroxide or Quil®-A aluminum hydroxide; liposomes; iscom adjuvant; mycobacterial cell wall extract; synthetic glycopeptides such as muramyl dipeptides or other derivatives; Avridine; Lipid A; dextran sulfate; DEAE-Dextran or DEAE-Dextran with aluminum phosphate; carboxypolymethylene, such as Carbopol®; ethylene malelic anhydride (EMA); acrylic copolymer emulsions such as Neocryl® A640 (e.g. U.S. Pat. No. 5,047,238); vaccinia or animal poxvirus proteins; subviral particle adjuvants such as orbivirus; cholera toxin; dimethyldiocledecylammonium bromide; or mixtures thereof.

Individual genetically altered virions may be mixed together for vaccination. Furthermore, the virus may be mixed with additional inactivated or attenuated viruses, bacteria, or fungi such as feline leukemia virus, feline panleukopenia virus, feline rhinotracheitis virus, feline calicivirus, feline infectious peritonitis virus, feline *Chlamydia psittaci, Microsporum canis,* or others. In addition, antigens from the above-cited organisms may be incorporated into combination vaccines. These antigens may be purified from natural sources or from recombinant expression systems, or may comprise individual subunits of the antigen or synthetic peptides derived therefrom.

The produced vaccine can be administered to cats by subcutaneous, intramuscular, oral, intradennal, or intranasal routes. The number of injections and their temporal spacing may be varied. One to three vaccinations administered at intervals of one to three weeks are usually effective.

The efficacy of the vaccines of the present invention is assessed by the following methods. At about one month after the final vaccination, vaccinates and controls are each challenged with 3–20 cat $ID_{50}$ units, preferably 5 cat $ID_{50}$ units of FIV, preferably the NCSU-1 isolate (ATCC accession number VR 2333). Whole blood is obtained from the animals immediately before challenge, and at intervals after challenge, for measurement of a) viremia and b) relative amounts of CD4 and CD8 lymphocytes.

Viremia is measured by isolating mononuclear cells from the blood, and co-culturing the cells with mononuclear cells from uninfected animals. After 7 days of culture, the culture supernatants are tested for FIV by enzyme-linked immunoassay (See Example 3 below).

The ratio of CD4 to CD8 lymphocytes in the circulation of vaccinates and controls is taken as a measure of immune function. Typically, FIV infection causes an inversion of the normal CD4:CD8 ratio of about 1.5–4 to a pathological ratio of about 0.5–1. The titers of CD4 and CD8 lymphocytes are measured by flow cytometry using specific antibodies (see Example 3 below).

Another measure of immune function is to challenge vaccinates and controls with *Toxoplasma gondii* at 6 months –12 months after the final vaccination. Normally, the severity of *T. gondii*-induced disease symptoms is considerably exacerbated in FIV-infected cats relative to uninfected cats. The severity of the *T. gondii* effect is determined by scoring ocular discharge, nasal discharge, dyspnea, and fever.

It will be understood that amelioration of any of the symptoms of FIV infection is a desirable clinical goal. This includes a lessening of the dosage of medication used to treat FIV-induced symptoms.

The following examples are intended to illustrate the present invention without limitation thereof.

Example 1

Preparation of p10 Deleted FIV Strain

1. Isolation of Parental DNA

Purified lambda DNA containing the full length proviral sequence for the NCSU-1 isolate is prepared with Wizard Lambda Preps DNA Purification System (Promega Corporation, Madison, Wis.) and is used as the parental DNA for constructing deletion mutants. DNA digestion, ligation and other molecular techniques are performed as described (Sambrook et al., Molecular Cloning: A Laboratory Manual, 2nd ed. Cold Spring Harbor Laboratory, 1989).

B. Preparation of FIV-Left Plasmid

Purified lambda DNA is digested with SalI to release the 11-kb insert DNA containing the full length FIV proviral sequence. The insert DNA is purified by the glass bead method using the GENECLEAN II kit from BIO 101, Inc. and digested with NcoI which cuts only once on the FIV genome, producing a 2.9 kb SalI-NcoI fragment, designated as fragment A, and a 8.1 kb NcoI-SalI fragment, designated as fragment B.

Fragment A is purified by glass bead method as above and subcloned into plasmid vector pGEM 5Zf(t) (Promega Corp., Madison, Wis.) to generate plasmid pFIV-left. The plasmid pFIV-left contains the left portion of the viral genome including the LTR, p15, p25 and p10 gene.

C. Deletion of p10 Sequence

Deletion of the two cysteine arrays within the p10 gene is facilitated by PCR-mediated mutagenesis using high-fidelity Pwo DNA polymerase according to the manufacturer's manual (Boehringer Mannheim, USA, Indianapolis, Ind.). The plasmid pFIV-left is used as the initial template for PCR reaction. SP6 primer and primer A are used to amplify 2.2-kb fragment C with sequence which ends at nucleotide 1124. The SP6 primer:

5'-TTAGGTGACACTATAGAATACTCAA-3' SEQ ID. NO. 1 anneals to the vector sequence upstream the SalI site. Primer A:

5'-GGTCCTGATCCTTTTGATTGCACTA-3' SEQ ID. NO. 2 anneals to the FIV sequence, nucleotides 1100 to 1124.

Primer B and T7 primer are used to amplify 0.6-kb fragment D which starts at nucleotide 1242. The primer:

5'-AAAGAATTCGGGAAACTGGAAGGCGG-3' SEQ ID. NO. 3 anneals within the gag p10 gene, nucleotides 1242 to 1267. The T7 primer:

5'-TAATACGACTCACTATAGGGCGAATTG-3' SEQ ID. NO. 4 anneals to the vector sequence downstream from the NcoI site.

The location for each GAG-specific primer is highlighted in FIGS. 2A–2E.

Fragment C and fragment D are purified as above, ligated and the ligation products are used as the template to amplify a 2.8-kb fragment using SP6 primer and T7 primer. The 2.8-kb fragment generated is purified as above and digested with SalI and NcoI to generate fragment E. Fragment E is identical to fragment A except the sequence for the segment spanning the two cysteine arrays is deleted, i.e. the sequence spanning nucleotides 1125 to 1241 is removed (see FIG. 1).

C. Construction of FIV delta p10 Plasmid

Fragment E and fragment B generated are purified as above. Then fragment E and fragment B are combined and cloned into the SalI site of the gene targeting vector pMC1neo Poly A (Stratagene, LaJolla, Calf.; Thomas, K. R., and Capecchi, M. R., Cell 51: 503–21, 1987), generating plasmid pFIV delta p10. The plasmid pFIV delta p10 contains the entire FIV genome with internal deletion within the p10 gene in addition to the neomycin resistance gene present on the gene targeting vector.

D. Production of Virions

Stable transfectants are obtained by transfecting the plasmid pFIV delta p10 into Vero cells (ATCC CCL 81), Crandell feline kidney cells (ATCC CCL 94) or AH927 feline embryonic fibroblast cells (Overbaugh et al., Virol. 188: 558–569, 1992) and selection by G418 by using cationic liposome-mediated transfection with the LIPOFECtamine® reagent and G418 (Genticin) according to the manufacturer's instruction (Life Technologies, Inc., Gaithersburg, Md.). Cultures of G418-resistant cells are tested for virus particle production by a) assaying the viral particle-associated reverse transcriptase activity; b) complementation plaque assay as described (Rein et al., J. Virol. 29: 494–500, 1979) to determine if the virus particles are able to initiate single cycle of infection; c) Western blotting using antiserum against the major core protein p25 (IDEXX, USA, Portland, Me.) to examine the integrity of the viral proteins; and d) direct examination of viral particles by electron microscopy.

The virus particles released from the stably transfected cells are to be examined for a) absence of viral RNA and DNA by RT-PCR and DNA PCR and b) absence of infectivity by the standard validated infectivity assays.

EXAMPLE 2

Preparation of Whole Killed Empty FIV Vaccines

Stably-transfected cells which produce non-infectious viral particles are grown on microcarriers in bioreactors or in roller bottles. Culture fluids are harvested at the time or multiple times when the viral particles reach high levels as determined by electron microscopy and/or the feline immunodeficiency virus antigen test kit (IDEXX, USA, Portland, Me.). The viral particles are inactivated by treatment with formalin or with binary ethylenimine, according to standard protocols well known in the art. Following inactivation, the viral particles are concentrated 10 to 50 fold with the hollow fiber procedure using a cut-off at molecular weight of 10,000 to 100,000 daltons. For preparing the vaccines, the concentrated fluids containing viral particles are mixed with immunologenically stimulating adjuvant, for example, ethylene maleic anhydride (EMA) 31, neocryl, MVP emulsigen, mineral oil, or adjuvant A or combination of several immunologenically stimulating adjuvants. Adjuvant A is an adjuvant comprising a block copolymer, such as a polyoxypropylene-polyoxyethylene (POP-POE) block copolymer, preferably Pluronic® L121 (e.g. U.S. Pat. No.

4,772,466), and an organic component, such as a metabolizable oil, e.g. an unsaturated turpin hydrocarbon, preferably squalane (2,6,10,15,19,23-hexamethyltetracosane) or squalene.

In this adjuvant mixture, the block copolymer, organic oil, and surfactant may be present in amounts ranging from about 10 to about 40 ml/L, about 20 to about 80 ml/L, and about 1.5 to about 6.5 ml/L, respectively. In a preferred embodiment of the stock adjuvant, the organic component is squalane present in an amount of about 40 mL/L, the surfactant is polyoxyethylenesorbitan monooleate (Tween®-80) present in an amount of about 3.2 ml/L, and the POP-POE block copolymer is Pluronic® L121 present in an amount of about 20 ml/L. Pluronic® L121 is a liquid copolymer at 15–40 C, where the polyoxypropylene (POP) component has a molecular weight of 3250 to 4000 and the polyoxyethylene (POE) component comprises about 10–20%, preferably 10%, of the total molecule.

Non-limiting examples of other suitable adjuvants include squalane and squalene (or other oils of animal origin); block copolymers such as Pluronic® (L121) Saponin; detergents such as Tween®-80; Quil® A, mineral oils such as Drakeol® or Marcol®, vegetable oils such as peanut oil; Corynebacterium-derived adjuvants such as corynebacterium parvum; Propionibacterium-derived adjuvants such as *Propionibacterium acne; Mycobacterium bovis* (Bacillus Calmette and Guerinn, or BCG); interleukins such as interleukin 2 and interleukin-12; monokines such as interleukin 1; tumor necrosis factor, interferons such as gamma interferon; combinations such as saponin-aluminum hydroxide or Quil® -A aluminum hydroxide; liposomes; iscom adjuvant; mycobacterial cell wall extract; synthetic glycopeptides such as muramyl dipeptides or other derivatives; Avridine; Lipid A; dextran sulfate; DEAE-Dextran or DEAE-Dextran with aluminum phosphate; carboxypolymethylene, such as Carbopol®; EMA; acrylic copolymer emulsions such as Neocryl® A640 (e.g. U.S. Pat. No. 5,047,238); vaccinia or animal poxvirus proteins; subviral particle adjuvants such as orbivirus; cholera toxin; dimethyldiocledecylammonium bromide; or mixtures thereof. The composition may also include a non-ionic detergent or surfactant, preferably a polyoxyethylene sorbitan monooleate such as a Tween® detergent, most preferably Tween®-80, i.e. polyoxyethylene (20) sorbitan monooleate.

Typically, 1 ml dose contains at least $10^6$ viral particles, as determined by electron microscopy or the feline immunodeficiency virus antigen test kit (IDEXX, USA, Portland, Me.).

Example 3

Test of Efficacy of Whole Killed Empty FIV Vaccines

A. Vaccination

Cats of age 8 weeks or greater are injected subcutaneously or intramascularly with the vaccine prepared above. Each cat receives two injections of vaccine at a 2–4 week interval. Two to six weeks following vaccination, the vaccinated cats and non-vaccinated cats are challenged by inoculating with 5 cat $ID_{50}$ of feline immunodeficiency virus (NCSU-1 isolate (ATCC VR 2333) and some other isolates). Antibody response to vaccination is measured by ELISA using a neutralizing peptide within the immunodominant region (V3) of the FIV envelope protein (Lombardi et al., J. Virol. 67:4742–49, 1993). Viral replication following challenging is monitored biweekly by a) determining the levels of FIV RNA or/+ proviral DNA with RT-PCR and DNA PCR; and/or b) by co-cultivation for presence of infectious virus particles.

1. Detection of Viremia a. PCR Detection of FIV proviral DNA

Mononuclear cells were isolated from whole blood using Percoll™ (Pharmacia Biotech, Piscataway N.J.) gradients. $5 \times 10^5$ cells were lysed and 1/10th of the lysate used in a polymerase chain reaction assay with oligonucleotide primers specific to the gag gene of FIV (TL Wasmoen et al. Vet. Immun. Immunopath. 35: 83–93, 1992) or the equivalent. FIV amplified DNA was detected by agarose gel electrophoresis and ethidium bromide staining or by enzyme linked oligonucleotide assays.

b. Tissue Culture Isolation of FIV

Culture isolate of FIV is performed as described previously (Wasmoen et al., Vet. Immuno. Immunopath. 35:83–93, 1992). Mononuclear cells are isolated from whole blood using Percol™ (Pharmacia Biotech, Piscataway N.J.) gradients. $5 \times 10^5$ cells from FIV-challenged cats were cultured with $1 \times 10^6$ mononuclear cells isolated from uninfected cats. Cultures are fed with RPMI media every 7 days and supernatant tested for the presence of FIV by an enzyme-linked immunosorbent assay (ELISA) that detects FIV p25 antigen (Petcheck ELISA, IDEXX, Portland, Me.). Alternatively, plasma can be used as the source of infectious virus.

2. Lymphocyte Subsets

Leukocytes are isolated from whole blood using Histopaque™ (Sigma Chemical Company, St. Louis Mo.) and lymphocyte subsets quantitated by staining the cells with antibodies specific to CD4 (monoclonal antibody CAT30A), CD8 (monoclonal antibody FLSM 3.357), pan T lymphocytes (monoclonal antibody FLSM 1.572) or B lymphocytes (anti-cat IgG) followed by FACS analysis. These monoclonal antibodies are described elsewhere (M.B. Tompkins et al. Vet. Immunol. Immunopathol. 26:305–317, 1990) and the flow cytometry procedure is the same as previously described (R.V. English et al. J. Infect. Dis. 170:543–552, 1994). CD4:CD8 ratios are calculated.

B. Toxoplasma gondii Challenge

Eight to twelve weeks following challenge with FIV, the cats are inoculated with 10,000 to 50,000 tacheozoites of *Toxoplasma gondii*. Tacheozoites of the ME49 strain of *T. gondii* that were frozen in 10% glycerol or oocyts were inoculated intraperitoneally into Swiss mice (Charles Rivers Laboratories) and serially passed in mice according to published procedures (Davidson et al., Am. J. Pathol. 143:1486, 1993). Tacheozoites harvested from peritoneal fluids of mice were enumerated using a hemacytometer. Cats were tranquilized using ketamine hydrochloride and inoculated with 50,000 fresh tacheozoites into the right common carotid artery that had been surgically isolated. Inoculation with Toxoplasma in this dosage generally causes mortality in up to 50% of cats which are FIV-infected and have not been vaccinated. Following Toxoplasma challenge, cats are monitored weekly for signs of clinical disease including ocular discharge, nasal discharge, dyspnea, fever, depression, and weight loss for 3 days prior to and up to 48 days following *T. gondii* inoculation.

Clinical signs follow *T. gondii* challenge were scored as follows:

| Clinical Sign | | Score |
|---|---|---|
| Fever | 103.0 to 103.9° F. | 1 point per day |
| | 104.0 to 104.9° F. | 2 points per day |
| | ≧105.0° F. | 3 points per day |
| (Temperatures were not scored until ≧1° F. above baseline.) | | |
| Depression/Lethargy | | 1 point per day |
| Dehydration | | 2 points per day |
| Nasal Discharge | | 1 point per day |
| Ocular Discharge | | 1 point per day |

| Clinical Sign | Score |
|---|---|
| Respiratory Distress: | |
| Tachypnea | 2 points per day |
| Dyspnea | 4 points per day |

It is expected that the vaccine prepared as described above will significantly reduce the appearance of clinical signs and mortality due to Toxoplasma infection.

What is claimed is:

1. A plasmid comprising an FIV genome, said genome having a deletion of a region encoding the nucleocapsid (p10) protein; said plasmid comprising:
   (a) a deletion of both of the nucleocapsid (p10) protein cysteine arrays, wherein said deletion encompasses nucleotides which result in the deletion of amino acids 14–52 of the FIV p10 protein upon translation,
   (b) a gag gene open reading frame, and
   (c) a gag-pol frameshift start site; and
   where upon transfection of said plasmid into host cells, said host cells have the properties of:
      (i) forming non-infectious virions and
      (ii) generating stable cell lines of said transfected host cells.

2. The plasmid of claim 1 wherein said deletion encompasses nucleotides 1126–1241 in SEQ ID NO: 5.

3. Host cells which are transfected with a plasmid comprising an FIV genome, said genome having a deletion of both of the nucleocapsid (p10) regions encoding the nucleocapsid (p10) protein cysteine arrays such that said cells produce FIV virions which do not comprise whole p10 nucleocapsid protein; said plasmid comprising:
   (a) a deletion of both of the nucleocapsid (p10) protein cysteine arrays, wherein said deletion encompasses nucleotides which result in the deletion of amino acids 14–52 of the FIV p10 protein upon translation,
   (b) a gag gene open reading frame, and
   (c) a gag-pol frameshift start site; and
   where upon transfection of said plasmid into host cells, said host cells have the properties of:
      (i) forming non-infectious virions; and
      (ii) generating stable cell lines of said transfected host cells.

4. The host cells of claim 3 which are selected from the group consisting of Vero cells (ATCC CCL 81), Crandell feline kidney cells (ATCC CCL 94), and AH927 feline embryonic fibroblast cells.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Bacteriophage SP6

(viii) POSITION IN GENOME:
      (B) MAP POSITION: SP6 primer
      (C) UNITS: bp (xi) SEQUENCE DESCRIPTION: SEQ ID NO:1:

TTAGGTGACA CTATAGAATA CTCAA                      25

(2) INFORMATION FOR SEQ ID NO:2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: feline immunodeficiency virus
      (C) INDIVIDUAL ISOLATE: NCSU-1

(viii) POSITION IN GENOME:
      (B) MAP POSITION: 1100-1124
      (C) UNITS: bp (xi) SEQUENCE DESCRIPTION: SEQ ID NO:2:

GGTCCTGATC CTTTTGATTG CACTA                      25

(2) INFORMATION FOR SEQ ID NO:3:

(i) SEQUENCE CHARACTERISTICS:
      (A) LENGTH: 26 base pairs
      (B) TYPE: nucleic acid
      (C) STRANDEDNESS: single
      (D) TOPOLOGY: linear

```
        (ii) MOLECULE TYPE: DNA (genomic)

(vi) ORIGINAL SOURCE:
             (A) ORGANISM: feline immunodeficiency virus
             (C) INDIVIDUAL ISOLATE: NCSU-1

(viii) POSITION IN GENOME:
             (B) MAP POSITION: 1242-1267
             (C) UNITS: bp (xi) SEQUENCE DESCRIPTION: SEQ ID NO:3:

AAAGAATTCG GGAAACTGGA AGGCGG                                              26

(2) INFORMATION FOR SEQ ID NO:4:

(i) SEQUENCE CHARACTERISTICS:
             (A) LENGTH: 27 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Bacteriophage T7

(viii) POSITION IN GENOME:
             (B) MAP POSITION: T7 primer
             (C) UNITS: bp (xi) SEQUENCE DESCRIPTION: SEQ ID NO:4:

TAATACGACT CACTATAGGG CGAATTG                                             27

(2) INFORMATION FOR SEQ ID NO:5:

(i) SEQUENCE CHARACTERISTICS:
             (A) LENGTH: 1353 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: feline immunodeficiency virus
             (C) INDIVIDUAL ISOLATE: NCSU-1

(viii) POSITION IN GENOME:
             (B) MAP POSITION: 1-1353
             (C) UNITS: bp (xi) SEQUENCE DESCRIPTION: SEQ ID NO:5:

ATGGGGAATG GACAGGGGCG AGATTGGAAA ATGGCCATTA AGAGATGTAG TAATGCTGCT          60

GTAGGAGTAG GGGGGAAGAG TAAAAAATTT GGGGAAGGGA ATTTCAGATG GCCATTAGA         120

ATGGCTAATG TATCTACAGG ACGAGAACCT GGTGATATAC CAGAGACTTT AGATCAACTA        180

AGGTTGGTTA TTTGCGATTT ACAAGAAAGA AGAAAAAAAT TTGGATCTTG CAAAGAAATT        240

GATAAGGCAA TTGTTACATT AAAAGTCTTT GCGGCAGTAG GACTTTTAAA TATGACAGTG        300

TCTTCTGCTG CTGCAGCTGA AAATATGTTC ACTCAGATGG GATTAGACAC TAGACCATCT        360

ATGAAAGAAG CAGGAGGAAA AGAGGAAGGC CCTCCACAGG CATTTCCTAT TCAAACAGTA        420

AATGGAGTAC CACAATATGT AGCACTTGAC CCAAAAATGG TGTCCATTTT TATGGAAAAG        480

GCAAGAGAAG GATTAGGAGG TGAGGAAGTT CAGCTATGGT TCACTGCCTT CTCTGCAAAT        540

TTAACACCTA CTGACATGGC CACATTAATA ATGGCCGCAC CAGGGTGCGC TGCAGATAAA        600

GAAATATTGG ATGAAAGCTT AAAGCAACTT ACTGCAGGAT ATGATCGTAC ACATCCCCCT        660
```

-continued

```
GATGCTCCCA GACCATTACC CTATTTTACT GCAGCAGAAA TTATGGGTAT TGGATTTACT      720

CAAGAACAAC AAGCAGAAGC AAGATTTGCA CCAGCTAGGA TGCAGTGTAG AGCATGGTAT      780

CTCGAGGGAC TAGGAAAATT GGGCGCCATA AAAGCTAAGT CTCCTCGAGC TGTGCAGTTA      840

AGACAAGGAG CTAAGGAAGA TTATTCATCC TTTATTGACA GATTGTTTGC CCAAATAGAT      900

CAAGAACAAA ATACAGCTGA AGTTAAGTTA TATTTAAAAC AGTCATTAAG CATGGCTAAT      960

GCTAATGCAG AATGTAAAAA GCCAATGACC CACCTTAAGC CAGAAAGTAC CCTAGAAGAA     1020

AAGTTGAGAG CTTGTCAAGA AATAGGCTCA CCAGGATATA AAATGCAACT CTTGGCAGAA     1080

GCTCTTACAA AAGTTCAAGT AGTGCAATCA AAAGGATCAG GACCAGTGTG TTTTAATTGT     1140

AAAAAACCAG GACATCTAGC AAGACAATGT AGAGAAGTGA GAAATGTAA TAAATGTGGA     1200

AAACCTGGTC ATGTAGCTGC CAAATGTTGG CAAGGAAATA GAAAGAATTC GGGAAACTGG     1260

AAGGCGGGGC GAGCTGCAGC CCCAGTGAAT CAAGTGCAGC AAGCAGTAAT GCCATCTGCA     1320

CCTCCAATGG AGGAGAAACT ATTGGATTTA TAA                                   1353
```

(2) INFORMATION FOR SEQ ID NO:6:

(i) SEQUENCE CHARACTERISTICS:
        (A) LENGTH: 450 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: feline immunodeficiency virus
        (C) INDIVIDUAL ISOLATE: NCSU-1

(xi) SEQUENCE DESCRIPTION: SEQ ID NO:6:

```
Met Gly Asn Gly Gln Gly Arg Asp Trp Lys Met Ala Ile Lys Arg Cys
1               5                   10                  15

Ser Asn Ala Ala Val Gly Val Gly Gly Lys Ser Lys Lys Phe Gly Glu
            20                  25                  30

Gly Asn Phe Arg Trp Ala Ile Arg Met Ala Asn Val Ser Thr Gly Arg
        35                  40                  45

Glu Pro Gly Asp Ile Pro Glu Thr Leu Asp Gln Leu Arg Leu Val Ile
    50                  55                  60

Cys Asp Leu Gln Glu Arg Arg Lys Lys Phe Gly Ser Cys Lys Glu Ile
65                  70                  75                  80

Asp Lys Ala Ile Val Thr Leu Lys Val Phe Ala Ala Val Gly Leu Leu
                85                  90                  95

Asn Met Thr Val Ser Ser Ala Ala Ala Glu Asn Met Phe Thr Gln
            100                 105                 110

Met Gly Leu Asp Thr Arg Pro Ser Met Lys Glu Ala Gly Gly Lys Glu
        115                 120                 125

Glu Gly Pro Pro Gln Ala Phe Pro Ile Gln Thr Val Asn Gly Val Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Pro Thr Asp Met Ala Thr Leu Ile Met Ala
            180                 185                 190

Ala Pro Gly Cys Ala Ala Asp Lys Glu Ile Leu Asp Glu Ser Leu Lys
        195                 200                 205
```

-continued

```
Gln Leu Thr Ala Gly Tyr Asp Arg Thr His Pro Pro Asp Ala Pro Arg
    210                 215                 220

Pro Leu Pro Tyr Phe Thr Ala Ala Glu Ile Met Gly Ile Gly Phe Thr
225                 230                 235                 240

Gln Glu Gln Gln Ala Glu Ala Arg Phe Ala Pro Ala Arg Met Gln Cys
                245                 250                 255

Arg Ala Trp Tyr Leu Glu Gly Leu Gly Lys Leu Gly Ala Ile Lys Ala
            260                 265                 270

Lys Ser Pro Arg Ala Val Gln Leu Arg Gln Gly Ala Lys Glu Asp Tyr
        275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Met Ala Asn
305                 310                 315                 320

Ala Asn Ala Glu Cys Lys Lys Pro Met Thr His Leu Lys Pro Glu Ser
                325                 330                 335

Thr Leu Glu Glu Lys Leu Arg Ala Cys Gln Glu Ile Gly Ser Pro Gly
            340                 345                 350

Tyr Lys Met Gln Leu Leu Ala Glu Ala Leu Thr Lys Val Gln Val Val
        355                 360                 365

Gln Ser Lys Gly Ser Gly Pro Val Cys Phe Asn Cys Lys Lys Pro Gly
    370                 375                 380

His Leu Ala Arg Gln Cys Arg Glu Val Arg Lys Cys Asn Lys Cys Gly
385                 390                 395                 400

Lys Pro Gly His Val Ala Ala Lys Cys Trp Gln Gly Asn Arg Lys Asn
                405                 410                 415

Ser Gly Asn Trp Lys Ala Gly Arg Ala Ala Pro Val Asn Gln Val
            420                 425                 430

Gln Gln Ala Val Met Pro Ser Ala Pro Pro Met Glu Glu Lys Leu Leu
        435                 440                 445

Asp Leu
```

(2) INFORMATION FOR SEQ ID NO:7:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (vi) ORIGINAL SOURCE:
        (A) ORGANISM: feline immunodeficiency virus
        (C) INDIVIDUAL ISOLATE: NCSU-1

(xi) SEQUENCE DESCRIPTION: SEQ ID NO:7:

```
Lys Glu Phe Gly Lys Leu Glu Gly Gly Ala Ser Cys Ser Pro Ser Glu
1               5                   10                  15

Ser Ser Ala Ala Ser Ser Asn Ala Ile Cys Thr Ser Asn Gly Gly Glu
            20                  25                  30

Thr Ile Gly Phe Ile
        35
```